United States Patent [19]
Ohta et al.

[11] Patent Number: 5,169,601
[45] Date of Patent: Dec. 8, 1992

[54] IMMUNOLOGICAL AGGLUTINATION DETECTING APPARATUS WITH SEPARATELY CONTROLLED SUPPLEMENTARY LIGHT SOURCES

[75] Inventors: Masato Ohta; Naoki Ozawa; Yasuhiko Yokomori, all of Shizuoka, Japan

[73] Assignee: Suzuki Motor Corporation, Shizuoka, Japan

[21] Appl. No.: 516,101

[22] Filed: Apr. 27, 1990

[51] Int. Cl.$^5$ ..................... G01N 21/03; G01N 33/49
[52] U.S. Cl. .................................. 422/73; 422/82.05; 422/82.08; 422/82.09; 435/291; 356/440
[58] Field of Search ................... 422/73, 82.05, 82.08, 422/82.09; 356/432, 436, 440; 435/291

[56] References Cited

U.S. PATENT DOCUMENTS 4,448,534  5/1984  Wertz et al. ..................... 356/436
4,710,031  12/1987  Kelly et al. ..................... 356/440

FOREIGN PATENT DOCUMENTS 59-98708  6/1984  Japan .
61-8934  3/1986  Japan .
61-45479  12/1986  Japan .

Primary Examiner—James C. Housel
Assistant Examiner—Jan M. Ludlow
Attorney, Agent, or Firm—Flynn, Thiel, Boutell & Tanis

[57] ABSTRACT

An immunological agglutination detecting apparatus including an agglutination examination plate having one or more reaction vessels each provided with a bottom face of which at least a part is slanted. A light emitting source is arranged at one side of the agglutination examination plate. A light receiver is situated on the other side thereof. Respective images of the agglutination patterns formed on the bottom faces of the reaction vessels are focussed on the light receiver through individual lenses in order to detect, by an electrical device, the agglutination patterns which are formed by the shining light from the light emitting source. In the preferred embodiment, the light emitting source is one or more rows of primary point sources, each corresponding to a particular vessel in the plate, and one or more supplementary point sources adjacent the ends of the row or rows. The intensity of the primary and supplementary light sources can be separately adjusted.

10 Claims, 16 Drawing Sheets

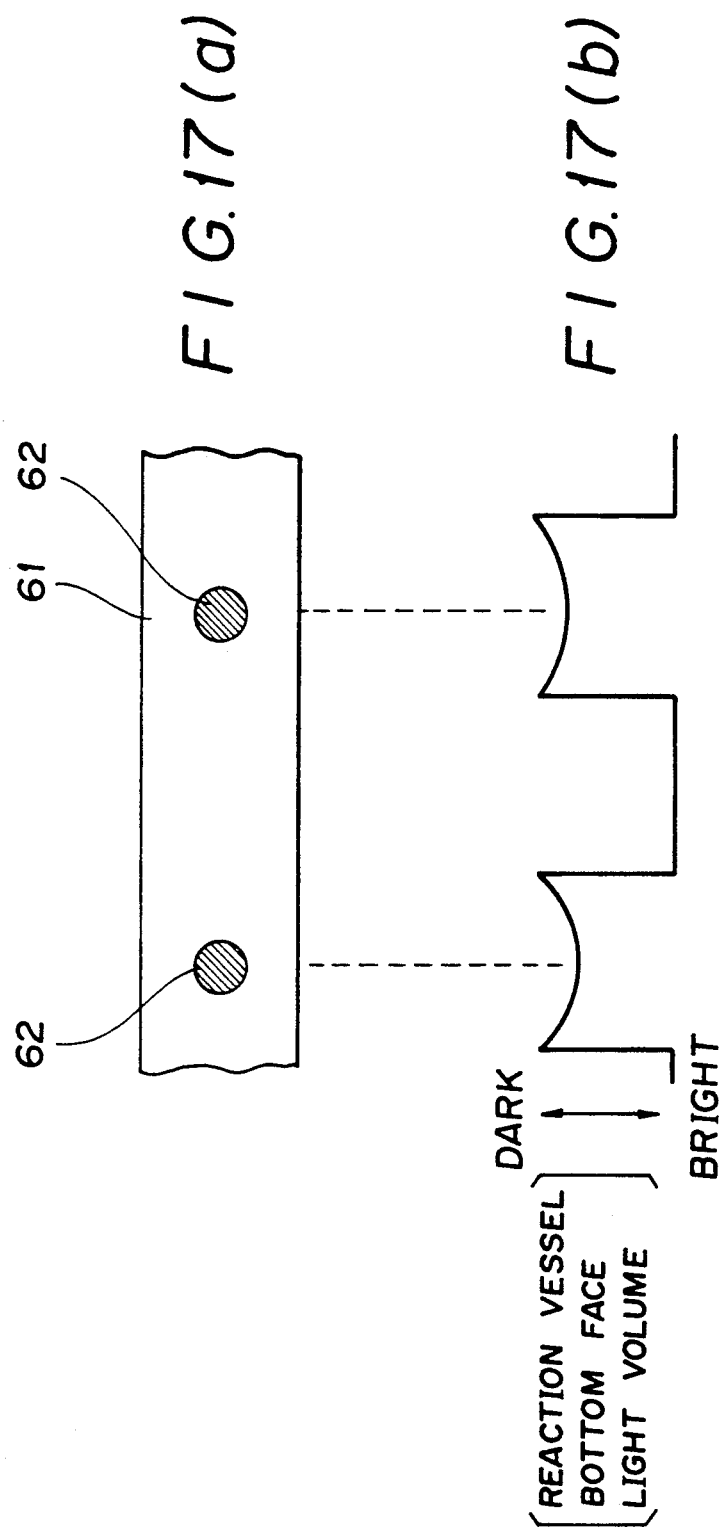

[LENS AND INCIDENT ANGLE]

[RELATIVE TRANSMISION RATIO WHEN THE CENTER IS 100%]

IMMUNOLOGICAL AGGLUTINATION DETECTING APPARATUS WITH SEPARATELY CONTROLLED SUPPLEMENTARY LIGHT SOURCES

CROSS REFERENCE TO RELATED APPLICATION

This application is related to copending application Ser. No. 07/516,118, filed Apr. 27, 1990, and titled "IMMUNOLOGICAL AGGLUTINATION DETECTING APPARATUS", naming inventors Yasuhiko YOKOMORI and Yukinori HARADA. The disclosure of this related application, which is owned by the same Assignee, is incorporated herein by reference.

FIELD OF THE INVENTION

This device relates to an immunological agglutination detecting apparatus, in particular, to an immunological agglutination detecting apparatus suitable to judge various blood types or group from the patterns of agglutination of blood cell particles or corpuscles and to detect antigens and antibodies.

BACKGROUND OF THE INVENTION

Recently, it has been widely used in the medical field to discriminate or judge the various agglutination patterns of blood cell particles, latex particles and carbon particles in order to detect and analyze various components or elements of blood (for example, blood type, various antibodies, various protein and the like) and virus.

The immunological agglutination detection apparatus for detecting such blood cell corpuscle agglutination or condensation patterns has been studied and developed in many fields and practiced in the products. For example, Japanese Utility Model publication No. 61-45479, Japanese Patent publication No. 61-8934, and Japanese Patent Laid-open No. 59-98708, respectively disclose some immunological agglutination detection apparatuses of such kind.

However, according to the immunological agglutination detection apparatus described in one of such conventional embodiments of Japanese Utility Model publication No. 61-45479, an image formed on the curved bottom face of a conical reaction vessel illuminated by a point light source is projected on a focus or image formation plane through a lens or an optical system. The conventional apparatus has a light receiving element placed at the image formation plane in order to receive an image scanned by a scanning mechanism and to convert the image to electrical signals progressively according to the intensity of light along the scanning direction. The light receiving element has an incident opening substantially identical to or smaller than the image of agglutination pattern formed at the center portion of the bottom face of the reaction vessel when it is non-agglutination, so that it is necessary to install a positioning mechanism for making the scanning light pass through the lowest portion (in which aggregations flock together) of the reaction vessel, resulting in a disadvantageously complicated structure. According to another shortcoming of the prior art, because the agglutination pattern obtained after being reacted changes according to the particular kind of the immunological agglutination of an examination item, it is necessary to adjust the open area, shape and the like of the slit or incident opening of the light receiving element. This is troublesome.

According to other embodiments or examples of such apparatuses described in Japanese Patent publication No. 61-8934 and Japanese Patent Laid-open No. 59-98709 above, a collimator lens as an illumination lens for making the light beams projected from a fixed point light source to parallel light flux is used, and the parallel light beam illuminates uniformly a microplate of the reaction vessel through a distribution plate (light diffusion plate) and the image on the conical bottom face of the reaction vessel is focussed on the light receiving face of the moving light receiving element. In consequence, it is necessary to determine at a light precision the relative position between the light source and the light receiving element. The conventional technology has such shortcomings as a low precision of the collimator lens and a too large structure of the illumination portion. In addition, the collimator lens is very expensive, resulting in a disadvantageously high price of the immunological agglutination detection apparatus.

It is a purpose of the device of this invention to provide an immunological agglutination detecting apparatus of small size and low cost without the shortcomings of the conventional technology or any deterioration in the result of examination.

According to the present device, it has an agglutination examination plate unit comprising a number of reaction vessels each having a slanted face of at least a part of the bottom face of the reaction vessel, the reaction vessels are arranged in the manner of a matrix (i.e. a grid) and formed on a base plate, a light source is placed at one side of the agglutination examination plate unit for projection therethrough, and a light receiving portion is situated at another side of the unit. Respective images of the agglutination patterns formed on the bottom faces of the plurality of the reaction vessels due to illuminous light outputted from the luminesce or light emitting portion are focussed on the light receiving face of the light receiving elements constituting the light receiving portion by means of lens, and as a result an output signal is adapted to detect the agglutination patterns. In addition, the light emitting portion above is constructed by at least one point light source associated with each respective reaction vessel of the plurality of reaction vessels in any column or file or a transverse row, which point light source is opposed to a respective reaction vessel. According to the construction of the light emitting portion, subsidiary point light sources are arranged at both ends of the row of these primary light sources.

The embodiment uses an ABO type judge or examination method of human blood, as an example, with respect to an immunological agglutination. In general, when the human being are classified by the blood group of ABO type, it is possible to divide it to four groups of A, B, AB, and O types.

In order to judge or decide respective blood groups in the blood type judge examination, it is general first to centrifugally separate the blood collected from a subject into red blood corpuscles and blood sera and then the blood type judgement is carried out. When respective red blood corpuscles and sera of four blood groups above are blended, respective corpuscles and sera are partly adhered to each other. The phenomenon of adhesion or agglutination above is shown in the following table.

TABLE 1

| Blood type | Agglutination due to red blood corpuscles and blood sera | | | |
|---|---|---|---|---|
| | Red blood corpuscles | | | |
| | O | A | B | AB |
| Blood sera O | X | O | O | O |
| A | X | X | O | O |
| B | X | O | X | O |
| AB | X | X | X | X |

In the above table, X shows non-agglutination and O shows agglutination which are occurred in the examination.

As apparent from the table above, the character of O type red blood corpuscles are differed from that of A, B, and AB types red blood corpuscles, and AB type red blood corpuscles have the characters of respective A and B types red blood corpuscles additionally.

According to the embodiment, two sample liquids are prepared by pouring dilution solutions into respective red blood corpuscles of each blood group and then anti A blood sera (B type blood sera) and anti B blood sera (A type blood sera) of examination agents are dropped into respective sample liquids in order to judge the blood type of the subject.

In this case, the blood type of the subject was A group and anti A blood sera was added to the blood, so as to carry out agglutination, and no condensation occurred. When the blood of the subject is not agglutinated by using anti A blood sera and agglutinated by anti B blood sera, it is B type. In case that it is agglutinated by using anti A blood sera and anti B blood sera, the blood type of the subject is of AB type. When it is not agglutinated by using both anti A and anti B blood sera, it is decided that it is of O type.

BRIEF DESCRIPTION OF THE DRAWINGS

FIG. 17($a$) is an explanatory view of the optical filter shown in FIG. 16, and FIG. 17($b$) is an explanation of a light reduction effect of the optical filter of FIG. 17($a$);

DETAILED DESCRIPTION

An embodiment of the invention will now be described with reference to FIGS. 1-10.

Figure 1:
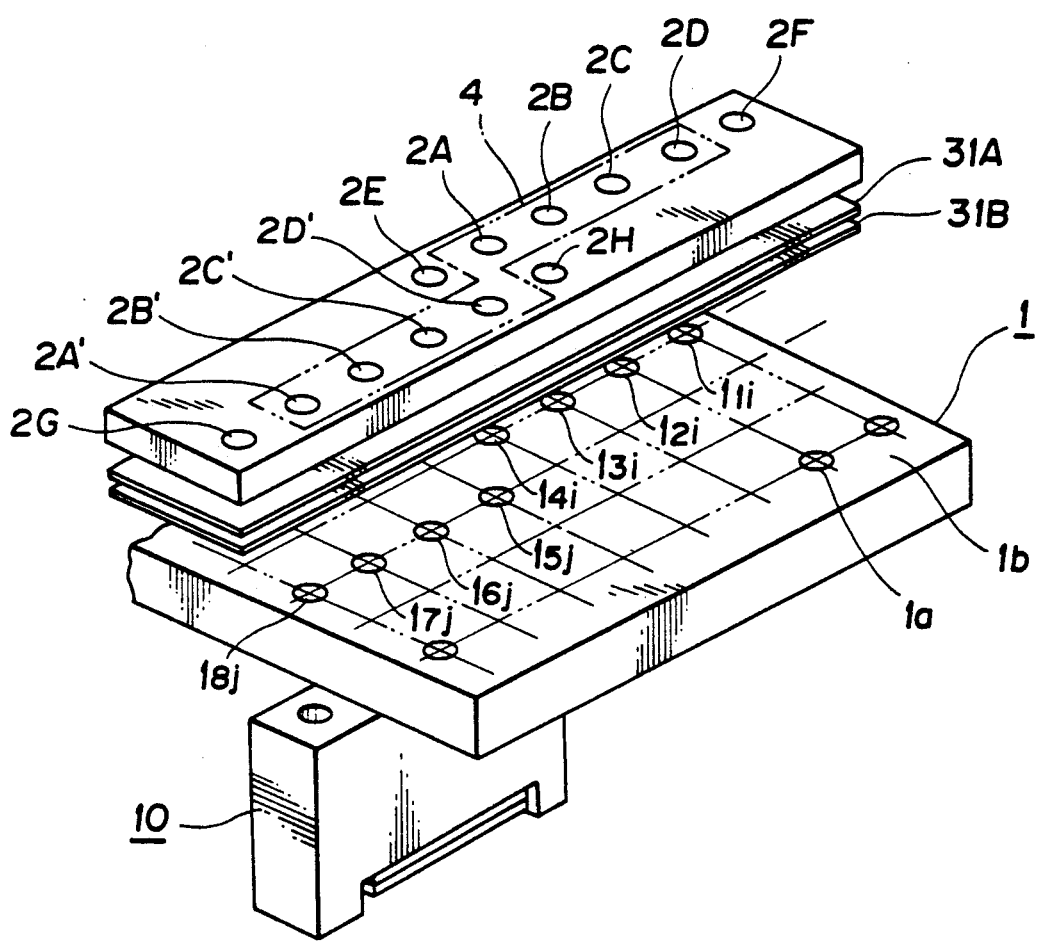
FIG. 1 is a construction view showing a major portion of an immunological agglutination detecting apparatus according to one embodiment of the present device.
Figure 2:
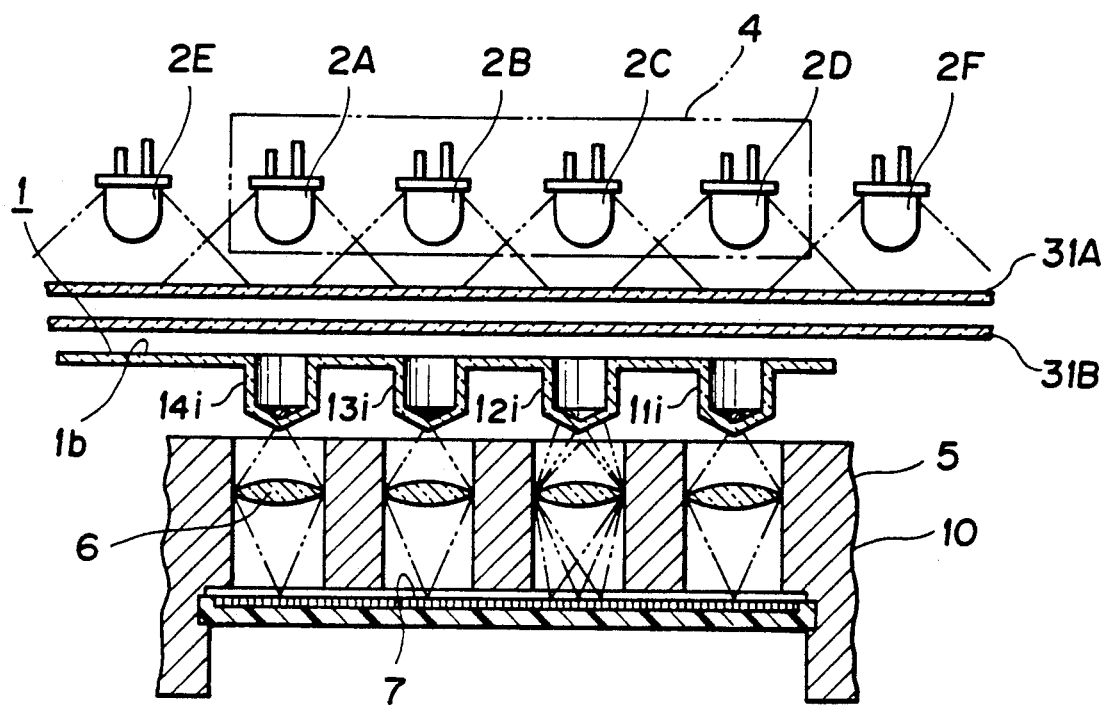
FIG. 2 shows the interior constructions of the light emitting portion and the light receiving portion shown in FIG. 1.

The immunological agglutination detecting apparatus shown in FIG. 1 includes a microplate 1 as an agglutination examination plate consisting of a number of reaction vessels 1$a$, respectively formed so as to have a conical shaped bottom plate as shown in FIG. 2, which reaction vessels are arranged in perpendicularly extending rows and columns which in effect define a matrix or grid configuration (see FIGS. 4, 5) on a transparent base plate 1$b$. A light emitting portion 4 is placed on a side (upper side in FIG. 1) for projection through the microplate 1, and a light receiving unit 10 constructed as a light receiving portion is placed on the other side (lower side in FIG. 1).

The light emitting portion 4 includes light emitting diodes 2D, 2C, 2B, 2A, 2D', 2C', 2B', 2A' defining primary point light sources, respectively placed opposed to reaction vessels 1$_{1i}$, 1$_{2i}$, 1$_{3i}$, 1$_{4i}$, 1$_{5j}$, 1$_{6j}$, 1$_{7j}$, 1$_{8j}$, forming any column (Column i, conveniently herein) and adjacent column (Column j, conveniently herein) of a number of reaction vessels arranged and formed on the microplate 1 in the manner of a matrix. In addition, the light emitting portion 4 has other light emitting diodes 2E, 2F, 2G, 2H defining supplemental point light sources, respectively arranged with respect to the end light emitting diodes 2A, 2D, 2A', 2D' so as to be disposed adjacent the opposite ends of each column of light emitting diodes 2D, 2C, 2B, 2A and 2D', 2C', 2B', 2A'. Between the light emitting portion 4 and the microplate 1, there are light distribution plates 31A, 31B, respectively arranged in parallel with the microplate 1 with a fixed gap or distance therebetween.

In accordance with the present device, it is possible to effectively prevent, owing to the particular structure thereof, the light volume or intensity at both the end portions of each column of light emitting diodes 2A, 2B ... from becoming less or weak, so that substantially uniform distribution and parallel light beams are shone on the microplate 1.

The light receiving unit 10 consists of a lens holder 5 provided with several convex lenses 6 arranged at regular intervals so as to oppose respective reaction vessels 1 and a primary CCD sensor 7 is held on the bottom of the lens holder 5 as shown in FIG. 2.

Figure 3:
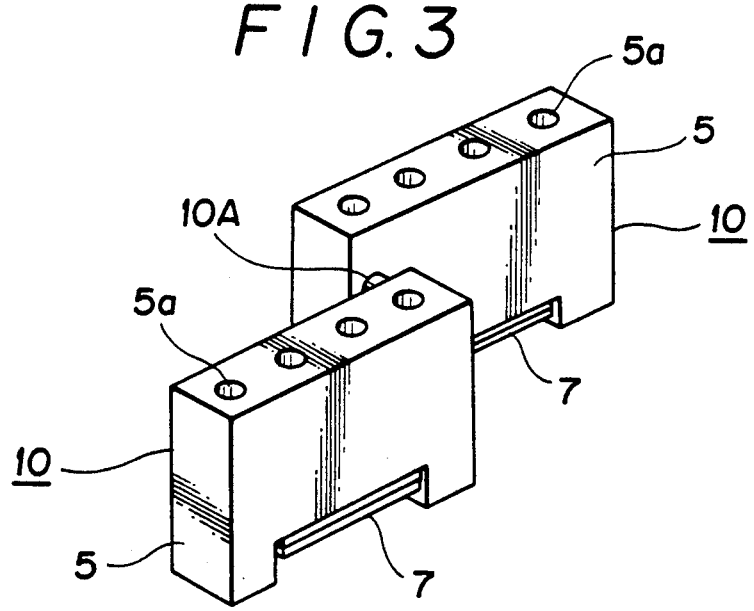
FIG. 3 is a perspective view of the light receiving unit shown in FIG. 1.

In detail, the lens holder 5 practically has an appearance as shown in FIG. 3 and a plurality of holes (four in this embodiment) arranged at the same distance as that between the reaction vessels 1a, 1a adjacent to each other along the longitudinal direction of the holder 5. At the peripheral walls of holes 5a, the convex lens 6 are fixed. On the bottom portion of the lens holder 5, the primary CCD sensor 7 is mounted at a fixed distance from the convex lens 6 equal to the focussing distance of the lens 6. The primary CCD sensor 7 is parallel with the microplate 1. As a result, respective images of agglutination pattern formed on the bottom faces of four reaction vessels $1_{1i}$, $1_{2i}$, $1_{3i}$, $1_{4i}$ in the Column i arranged in a matrix shape on the microplate 1, which images are formed by means of light outputted from the light emitting diodes 2A, 2B ... are adapted to be focussed on the primary CCD sensor 7 through the convex lenses 6. Thus, images of agglutination pattern formed at the bottom faces of four reaction vessels $1_{1i}$, $1_{2i}$, $1_{3i}$, $1_{4i}$ can be detected at one time through the primary CCD sensor 7. Because one convex lens 6 is held structurally in each hole 5a formed in the lens holder 5, substantially no effect of the light passed through the reaction vessel 1 adjacent to the hole is applied to each other.

In accordance with the embodiment above, two light receiving units 10 are used and respective units are arranged on the upper face of a moving plate 16 (FIG. 7) which will be described below so as to make respective longitudinal parts of the light receiving units 10 overlap one another along the reaction vessels $1_{1i}$, $1_{2i}$, $1_{3i}$, $1_{4i}$, $1_{5j}$, $1_{6j}$, $1_{7j}$, $1_{8j}$ of the Columns i and j.

Figure 4:
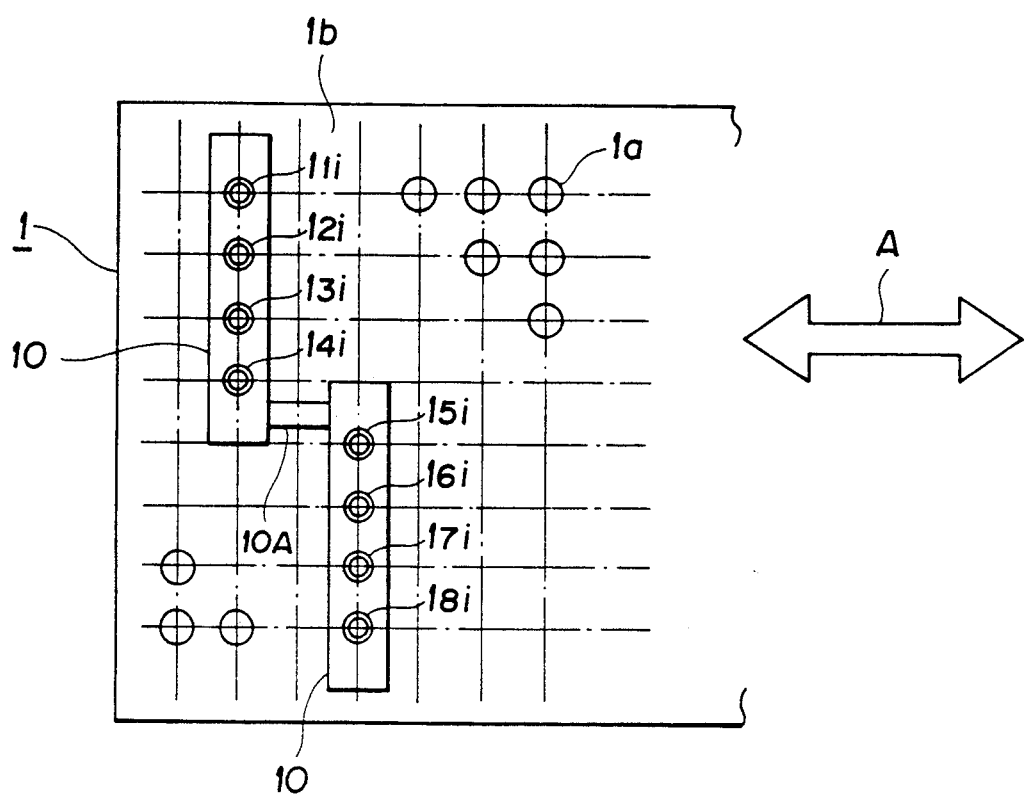
FIG. 4 is an explanation view showing an example of the arrangement of the light receiving unit shown in FIG. 1.
Figure 5:
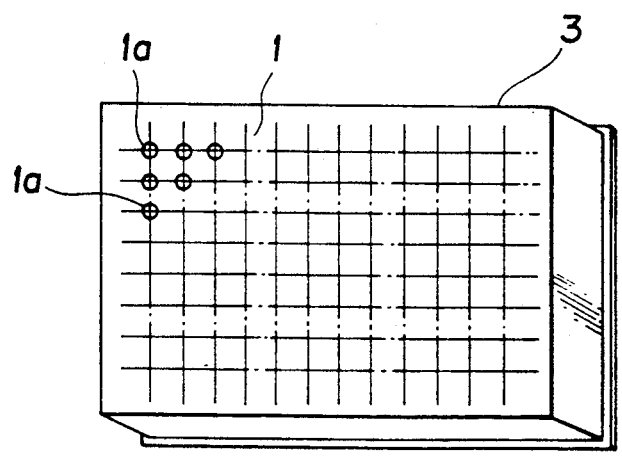
FIG. 5 is a view showing the whole structure of the microplate shown in FIG. 1.
Figure 6:
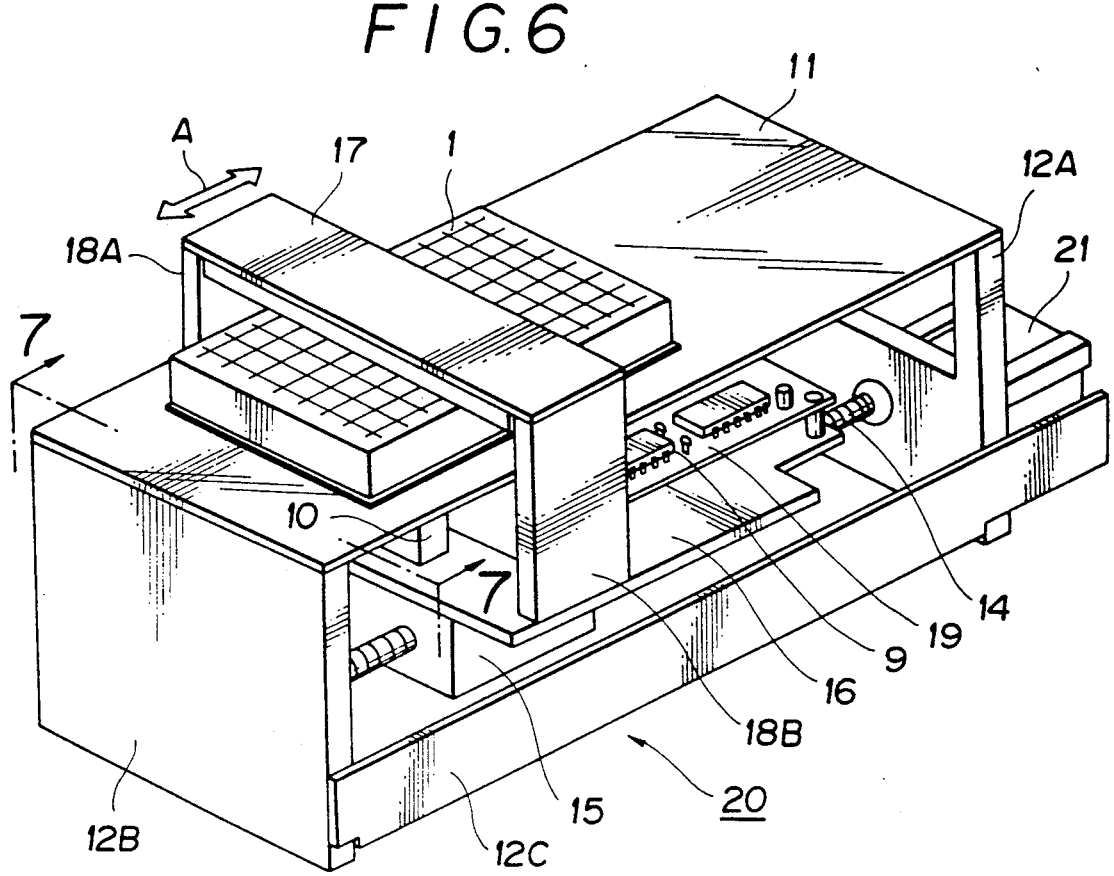
FIG. 6 is an outline perspective view showing the whole structure of the embodiment shown in FIG. 1.
Figure 7:
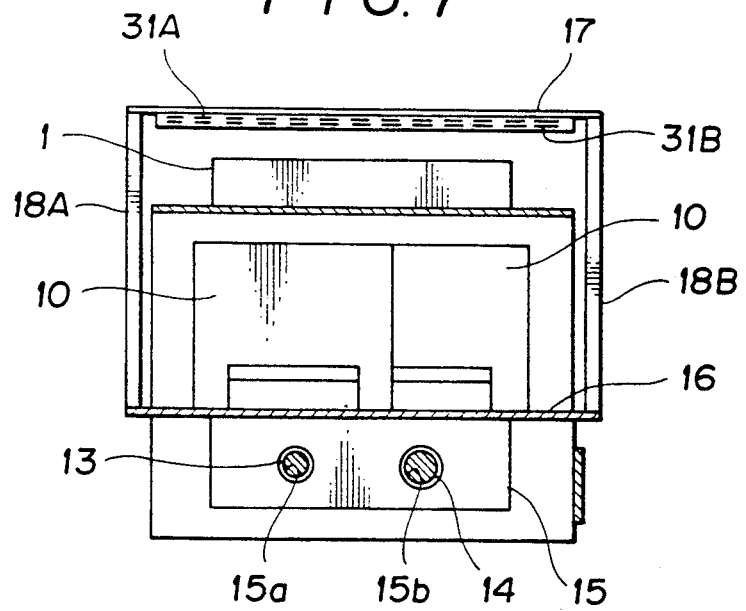
FIG. 7 is a sectional view taken along the line 7—7 of FIG. 6.
Figure 8:
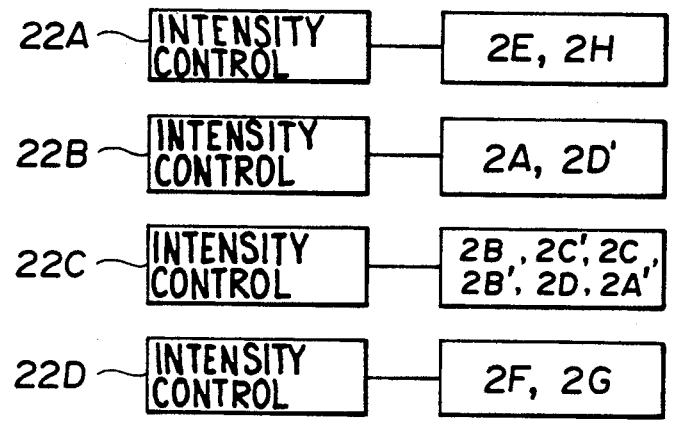
FIG. 8 is an explanation view of the relation between the light intensity control means and the light source shown in the embodiment of FIG. 1.

Practically, these light receiving units 10 and 10 are connected by a connector 10A shown in FIGS. 3 and 4. In consequence, these light receiving units 10 are arranged as shown in FIG. 4 so as to make the four holes 5a, 5a ... formed in each lens holder 5 at regular intervals identical to that between the reaction vessels adjacent to each other along the longitudinal direction of the holder 5 agree with the reaction vessels $1_{1i}$, $1_{2i}$, $1_{3i}$, $1_{4i}$, $1_{5j}$, $1_{6j}$, $1_{7j}$, $1_{8j}$. In this case, a number of reaction vessels 1a are arranged and formed in the microplate 1 in a matrix shape of eight (8) columns and twelve (12) rows (or files), and the microplate 1 with the reaction vessels 1a are mounted on a horizontal plate 11 (FIG. 6) made of transparent material, which horizontal plate 11 constitutes a part of the immunological agglutination detecting apparatus 20 as shown in FIG. 6.

The immunological agglutination detecting apparatus 20 of the present device has an end support member or wall 12A and another end support member or wall 12B supporting the horizontal top plate 11 from the bottom. There is a reinforcement plate 12C extending between these support members 12A and 12B so as to stably connect them to each other. A guide shaft 13 is installed on the immunological agglutination detecting apparatus 20 of the present device along the longitudinal direction of the horizontal plate 11, extending in the space between and supported on the support members 12A and 12B. In addition, another guide shaft 14 having a male thread engaged with a ball screw, which thread is formed along the whole length of the shaft, is rotatably supported on supports 12A and 12B and extends in parallel with the first guide shaft 13.

Both shafts 13, 14 have a box 15 mounted slidably and reciprocally thereon for movement along these shafts. The box 15 has a hole 15a having a diameter almost identical to that of the shaft 13 and a hole 15b having a diameter substantially identical to that of the shaft 14. In the interior of the box 15, there are female thread portions of a ball screw opposing the male thread portions through balls (not shown).

A moving plate 16 for mounting the light receiving unit 10 thereon is installed on the upper face of the box 15 so as to be parallel with the horizontal plate 11 and fixed thereto. Side support plates 18A and 18B support an upper plate 17 at both ends of the upper plate. These support plates are attached to opposite sides of the moving plate 16 at a right angle. The light emitting diodes 2A, 2B ... are fixed on the lower face of the upper plate 17. The light distribution plates 31A and 31B are held integrally on the lower face of the upper plate 17. There is a LED driver circuit (see FIG. 12) for driving the light emitting diodes 2A, 2B ... on the lower face of the upper plate 17. The LED driver circuit is constructed with electronic elements, such as IC and the like. According to the embodiment, the LED driver circuit also has light intensity control means 22A-22D for adjusting each light emitting diode 2A, 2B ... (see FIG. 8).

On the upper face of the moving plate 16, there is a base plate 19 fixedly arranged in parallel with the moving plate 16. The base plate 19 has a CCD driver circuit (see FIG. 12) for driving the primary CCD sensor 7, which circuit is constructed with, for example, IC and the like and is mounted on the base plate 19.

A motor 21 for rotating the shaft 14 through a gear set or mechanism (not shown) is installed outside of the support member 12A. In consequence, when the motor 21 starts, the moving plate 16 and the upper plate 17, respectively sandwiching the horizontal plate 11 and the microplate 1 from upward and downward, move integrally or as a unit along the direction of arrow A. In other words, these plates 16 and 17 are adapted to move reciprocally along the transverse rows of the reaction vessels 1a arranged on the microplate.

The primary CCD sensor 7 employed in the embodiment in a general-purpose primary CCD sensor. The sensor 7 has a light receiving face on which a plurality of photo electric converting elements of photo sensitivity are arranged in a line. Owing to the particular structure, the images of agglutination patterns formed on the bottom faces of the reaction vessels 1a, 1a ..., respectively are divided into five parts through a plurality of photoelectric converting elements and they are converted to electric signals through the elements according to the intensity of the light shone unto the sensor 7. According to the embodiment, the electric signals are sent to a CPU (not shown) through an analog/digital converter (not shown) as known in the conventional system in order to judge the agglutination pattern of the test sample.

The operation of the immunological agglutination detecting apparatus 20 constructed as mentioned above will be described with reference to the drawings.

First, before the detection of agglutination patterns, respective light intensity control means 22A, 22B ... are used to control volume or intensity of light. For example, in the condition of the apparatus shown in FIG. 1 and FIG. 4, some reaction vessels $1_{4i}$, $1_{5j}$ confronting the light emitting diodes 2A and 2D' are brighter than other reaction vessels because only these reaction vessels $1_{4i}$, $1_{5j}$ are shone from three light emitting diodes, so that the light intensity of these light emitting diodes 2A and 2D' is lowered as is simultaneously the light intensity of the light emitting diodes 2E and 2H as supplemental light sources. Next, the light intensities of the light emitting diodes 2B, 2C, 2D, 2A', 2B', 2C' are accordingly adjusted making these intensities of the same illumination and then the light emitting diodes 2F and 2G of the supplemental light sources are consequently controlled.

When the motor 21 is driven, the moving plate 16 starts its motion and a positioning means (not shown) controls the CPU (not shown). When the light receiving units 10, 10 shown in FIGS. 1 and 4 are moved to a position below any column of the reaction vessels 1a formed in the microplate 1 and stopped at that position, the light beams from the light emitting diodes 2A, 2B . . . are shone on the microplate 1 through the light distribution plates 31A and 31B. As a result of the shining above, respective images of agglutination patterns formed on the bottom faces of the eight illuminated reaction vessels, for example, vessels $1_{1i}, 1_{2i}, 1_{3i}, 1_{4i}, 1_{5j}, 1_{6j}, 1_{7j}, 1_{8j}$ . . . , are respectively placed received on the light receiving unit 10. The images which are formed by shining light from the light emitting diodes 2A, 2B . . . are focussed on the primary CCD sensor 7 by the respective convex lens 6. Output signals from the primary CCD sensors 7, 7 are sent to the CPU (not shown) through the analog/digital converter (not shown). The CPU calculates the distance moved or position of the moving plate 16 from the feeding volume or revolution number of the motor in order to determine the particular column of reaction vessels under examination, and then the agglutination pattern of the test sample in each reaction vessel is automatically judged.

One example of the judging process will be explained.

In the judging process of the ABO type blood group, blood cell particles are combined to each other or flocked together through blood sera in an agglutination phenomenon and are deposited uniformly on the conical bottom faces of the reaction vessels 1a looking like snow. When no agglutination has occurred, blood cell particles are scattered or separated and descend to the conical bottom faces of the reaction vessels, and then these separated particles roll down along the slant walls to the lower central portion of the bottom face for deposit there.

Figure 10:
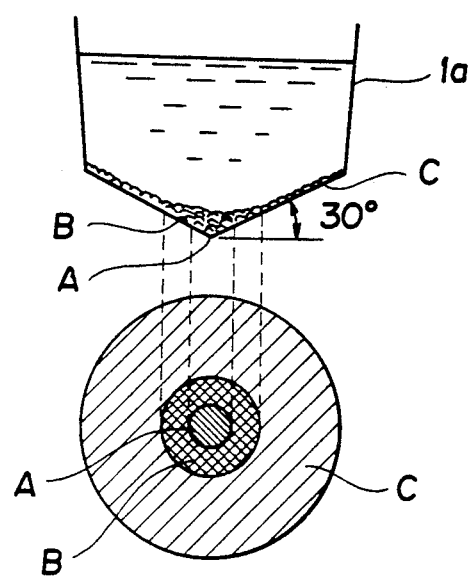
FIG. 10 is an explanation view of the operation of the embodiment shown in FIG. 1.

FIG. 10 shows an enlarge view of the bottom face of the reaction vessel 1a. The radius of the bottom face of the reaction vessel 1a is 6 mm, the depth of the slanted portion is 1.5 mm, and the slant angle is 30 degree. FIG. 10 shows the condition of the blood cell particles agglutinated or flocked together on the bottom face and deposited uniformly thereon. Such uniform deposition pattern can be attained in, for example, the ABO type blood group judging examination process, by adding anti A blood sera (B type blood sera) to A type subject (red blood corpuscles) suspension liquid letting them descend naturally or gravitationally. In detail, when the red blood corpuscles are uniformly deposited as described above, these corpuscles are adhered to each other through blood sera, so that there is substantially no rolling-down phenomenon of the red blood corpuscles along the slanted face of the reaction vessel and, on the contrary, they are deposited uniformly on the bottom face.

Seeing in detail the deposition pattern, it is apparent that considerable thick deposition is recognized near a central lowest point A, and, however, rather thin deposition is seen on a peripheral portion C. On the middle portion B between the portion C and the point A, the thickness varies gradually and continuously.

Accordingly, light transmission volume is the smallest at the point A, it increases gradually toward the peripheral portion C, and reaches its largest adjacent the peripheral portion C of the reaction vessel 1a. Resultantly, the output of the primary CCD sensor 7 changes according to the particular condition of the light transmission volume, so that the CPU judges that it is of a uniform deposition pattern of the A type blood group of the subject.

Figure 11:
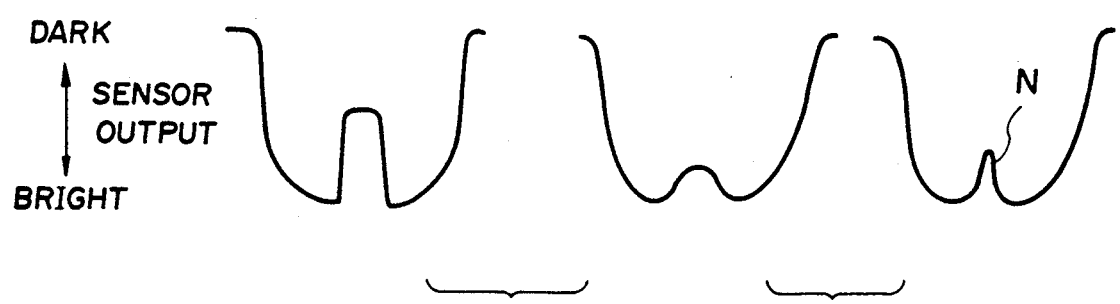
FIG. 11 shows examples of output patterns.

FIG. 11 depicts the images of agglutination patterns focussed on the light receiving face of the primary CCD sensor 7 and the output of the sensor 7 when such condensation patterns described above are generated. The leftmost diagram is an output corresponding to the pattern when no agglutination occurs, the center diagram depicts an output corresponding to the uniform deposit pattern, and the rightmost diagram is an output pattern of a vacant bottom face of an empty reaction vessel.

As described above and shown in FIGS. 3 and 4, in accordance with the embodiment of the present device, two light receiving units 10 are connected through their longitudinally overlapped parts by means of the connecting member 10A making a crank shape of them and accordingly the primary CCD sensors 7 as mounted to the bottom faces of the light receiving units 10 are arranged or positioned along the columns of the reaction vessels 1a so that it is possible to simultaneously detect several light images, at one time, of agglutinations in one column, which images are formed on the bottom faces of the reaction vessels 1a situated in a matrix shape on the microplate 1. Resultantly, it is possible to detect the agglutination of the subjects or test samples in all reaction vessels 1a of the microplate 1 by scanning along a single direction, and the positioning precision can be improved, so that advantageously the examination time of the reaction vessels 1a can be considerably shortened relative to the case in which both transverse and longitudinal directional scanning are necessary. Also, it is very easy to create and control the light intensity shone on respective reaction vessels 1a due to the function of the supplemental light emitting diodes 2E, 2F, 2G, 2H as situated at both ends of the columns of primary light emitting diodes 2A, 2B . . . Because no illuminous lens is employed in the detecting apparatus, it is possible to decrease the manufacturing cost of the apparatus by the cost of the lens and accordingly to miniaturize the whole size of the apparatus. In addition, because light emitting diodes are employed as light sources in the apparatus, there is attained improved reliability, stability, and lower consumption of energy.

Figure 9:
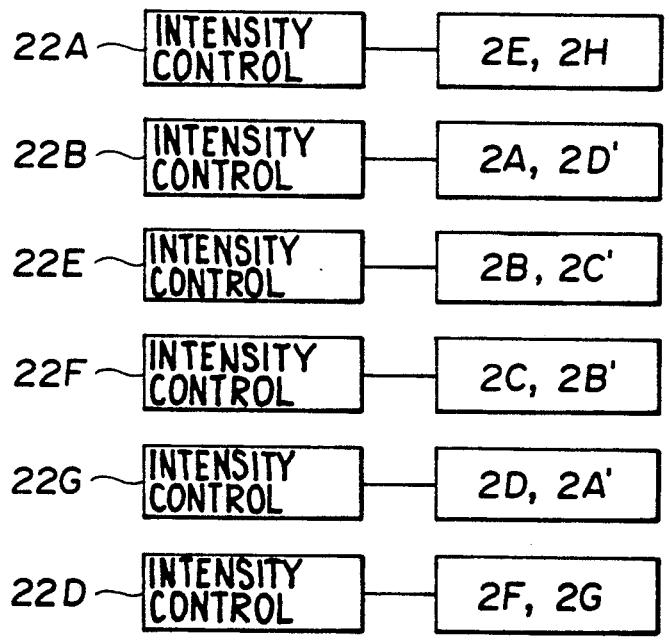
FIG. 9 is another explanation view of a relation similar to FIG. 8.

It is possible to employ light adjusting means 22E, 22F, 22G shown in FIG. 9 in place of the light volume or intensity control means 22C in order to divide the control function of the light intensity control means 22C into three separate functions, making it possible to control the intensity more precisely.

Because the immunological agglutination detecting apparatus of the present device is constructed and functions as above, it is possible to shine light of uniform illumination to respective reaction vessels formed in the agglutination examination plate of the detecting apparatus, without any illuminous lens, as in prior devices. Consequently, it is possible to omit from the apparatus any illuminous lens, such as collimeter lens, without any decrease of credibility on the examination result. Thus, the optical system can be simplified and the apparatus can be miniaturized, reducing the manufacturing cost of the apparatus.

A second embodiment of the immunological agglutination detecting apparatus will be explained with reference to FIGS. 12 and 13. Corresponding parts of this embodiment are identified by the same reference numbers used to identify the parts of the first-described embodiment.

Figure 12:
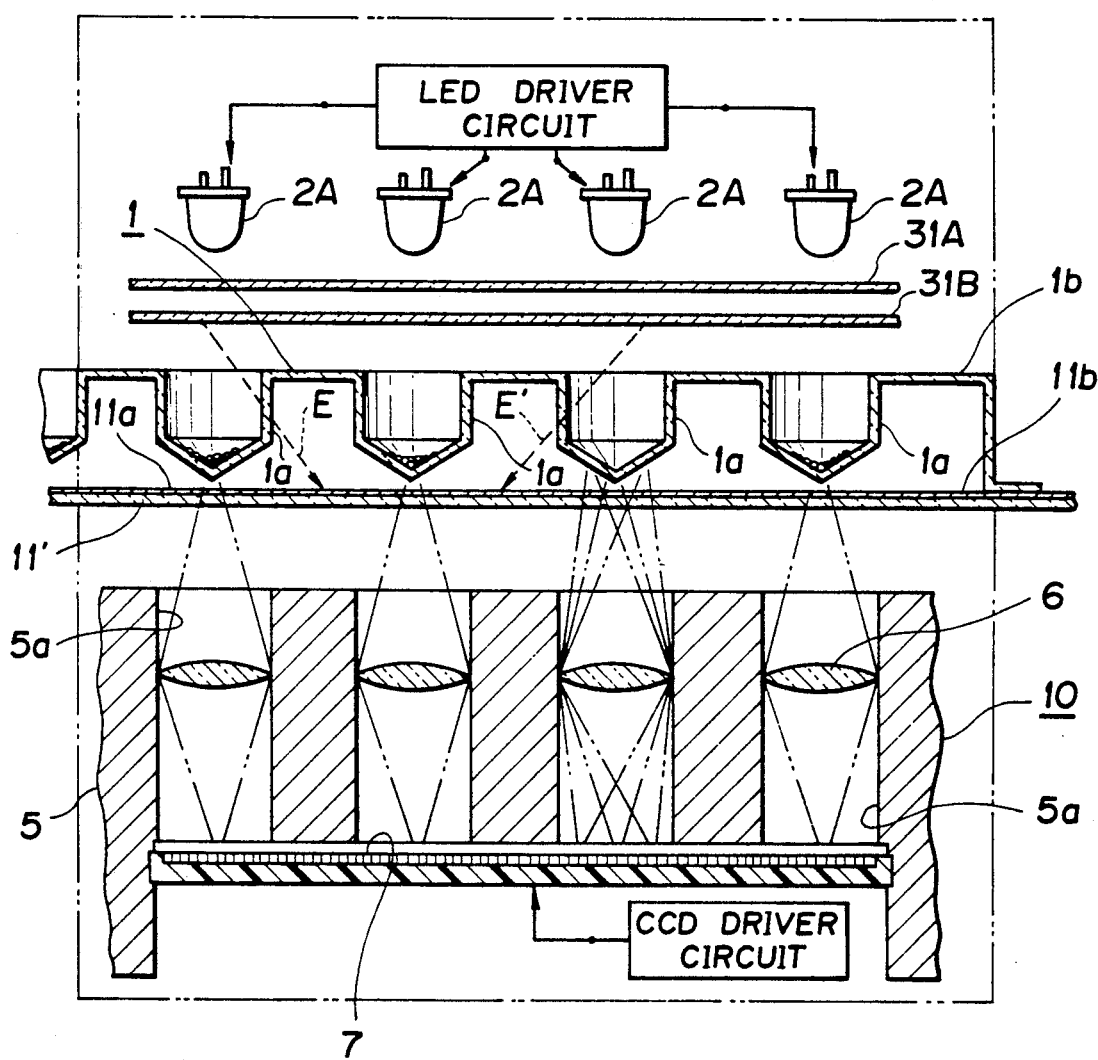
FIG. 12 is a concept view depicting the structure of a second embodiment of the invention.
Figure 13:
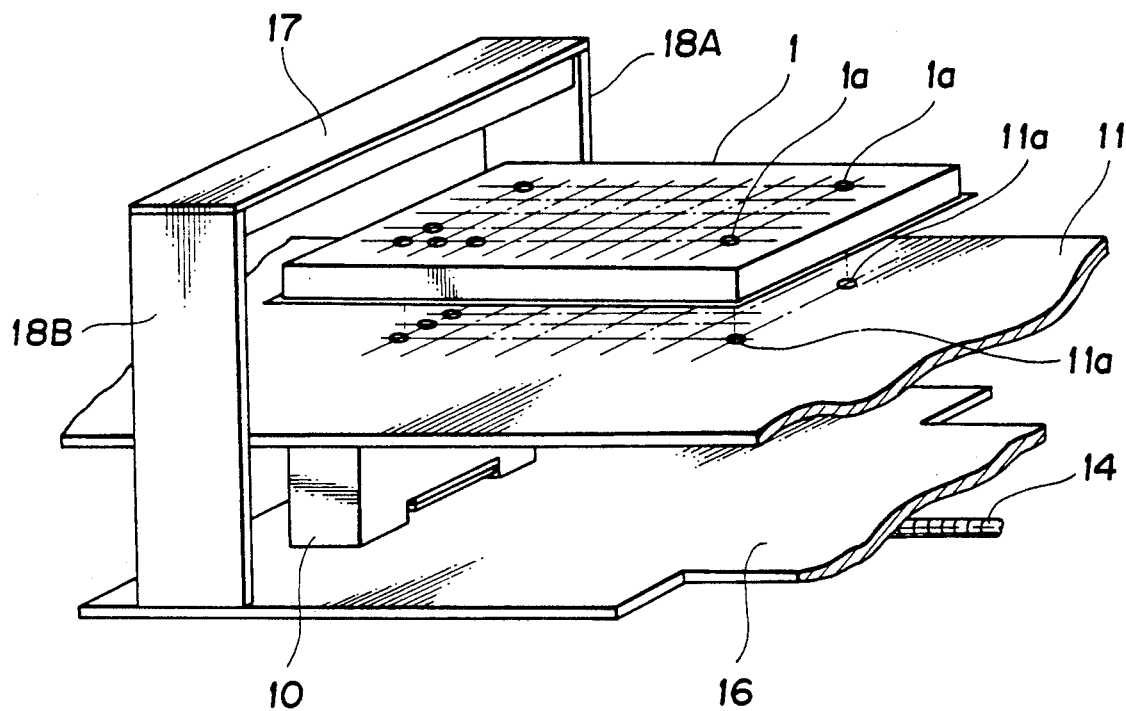
FIG. 13 is a view of the horizontal plate shown in FIG. 12 and an explanation view depicting the positional relationship between the windows and the reaction vessels.

The apparatus shown in FIG. 12 has a microplate unit 1 of an agglutination examination plate consisting of a light transmittable base plate 1b and a plurality of reaction vessels, each designated 1a for convenience, arranged in a grid-like or matrix shape and having conical bottom faces. A row of light emitting diodes, each designated 2A for convenience, of a light emitting means is arranged at one side of the microplate 1 (at the upper side in FIG. 12), and the primary CCD sensor 7 of a light receiving means is arranged at the other side thereof (at the lower side in FIG. 12). Between the light emitting diodes 2A, 2A . . . and the plate 1, light distribution plates 31A and 31B are placed so as to be parallel to the plate 1 with a fixed distance therebetween. In consequence, substantially uniform and parallel light beams are shone unto the microplate 1. Between the microplate 1 and the primary CCD sensor 7, there is a single convex lens 6 correspondingly to each reaction vessel 1a.

The convex lenses 6 are held in a lens holder 5 which has a plurality (four in this embodiment) of holes 5a, 5a . . . separated at a regular distance identical to that between adjacent reaction vessels 1a, 1a and arranged along the longitudinal direction of the lens holder 5. Respective convex lenses 6 are secured to the interior wall of each hole 5a. At the bottom portion of the lens holder 5, there is the primary CCD sensor 7 vertically separated by a fixed distance from the convex lens 4, which distance is substantially identical to the focal distance of the convex lens 4. Sensor 7 is parallel to the microplate 1.

In addition, according to this embodiment, a horizontal light-preventing mask plate 11', respectively having a single light transmittable window 11a corresponding to each reaction vessel 1a of the microplate 1, is placed adjacent to the microplate 1.

Practically, as shown in FIG. 12, the horizontal mask plate 11' constitutes a part of the horizontal top plate 11 shown in FIG. 6, and the microplate 1 is mounted thereon. The microplate 1 has a plurality of reaction vessels 1a, 1a. . . arranged thereon in a matrix of eight (8) columns and twelve (12) rows or files, such arrangement being shown in FIG. 5. The windows 11a, 11a . . . through which light passes are formed in the part 11' of horizontal plate 11, respectively at matrix locations corresponding to the reaction vessels 1a, 1a . . .

The diameter of the light passing windows 11a is a little smaller than the diameter of the reaction vessel 1a, however, but is large enough for the light from the respective reaction vessel 1a to pass therethrough (see FIG. 12).

Preferably the horizontal plate 11 including part 11' is wholly made of transparent plastic material and a light preventing seal plate or film 11b having said windows 11a therein is adhered to the plate 11 in order to prevent light from transmitting through the portion of the horizontal plate other than the windows. It is possible, in place of applying the seal 11b, to color the necessary parts of the horizontal plate 11, or to manufacture the windows 11a by transparent glass panes or resin and other portions by shading material and then combining them. Also a so-called optical filter can be used for the purpose.

The remaining construction of this second embodiment substantially corresponds to the first-described embodiment.

According to this embodiment of the invention, the light prevention shield or film 11b having windows 11a is adhered to the transparent member defining the horizontal plate 11, so that it is possible to effectively prevent light, other than that passing through the reaction vessels, from entering into the convex lens 6 (see arrows E, E' in FIG. 11), thus improving the examination precision of the test samples.

Because the light emitting diodes 2A and the primary CCD sensor 7 are adapted to integrally move in a fixed positional relationship, it is possible to further improve the examination precision. In addition, because the microplate 1 is of a stationary type, agglutinated and deposited corpuscles in the reaction vessel 1a are not subjected to vibration and other disadvantageous effects leading to distribution of them, so that the reaction result can be preferably sustained stably. Even though foreign matters are accidentally dropped on the apparatus before mounting the microplate 1, the horizontal plate 11 prevents the foreign matters from invading the lens holder 5 and the convex lens 6, and the ball screw portion for driving the optical system of the apparatus.

A third embodiment will now be described referring to FIGS. 14 and 15. The same reference numbers will be used to designate the same structural members of the third embodiment as that of the second embodiment.

Figure 14:
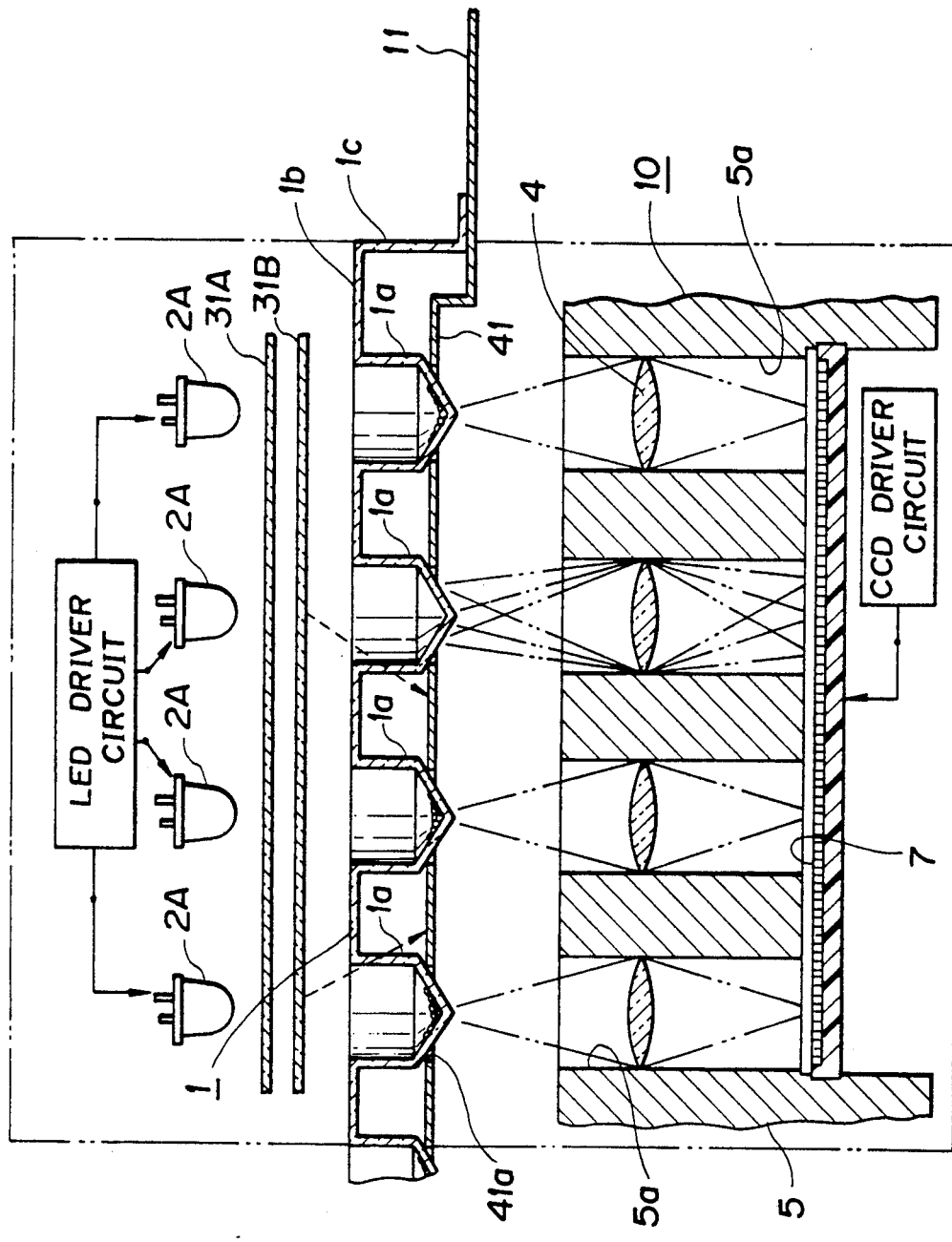
FIG. 14 is a concept view depicting the structure of a third embodiment of the invention.
Figure 15:
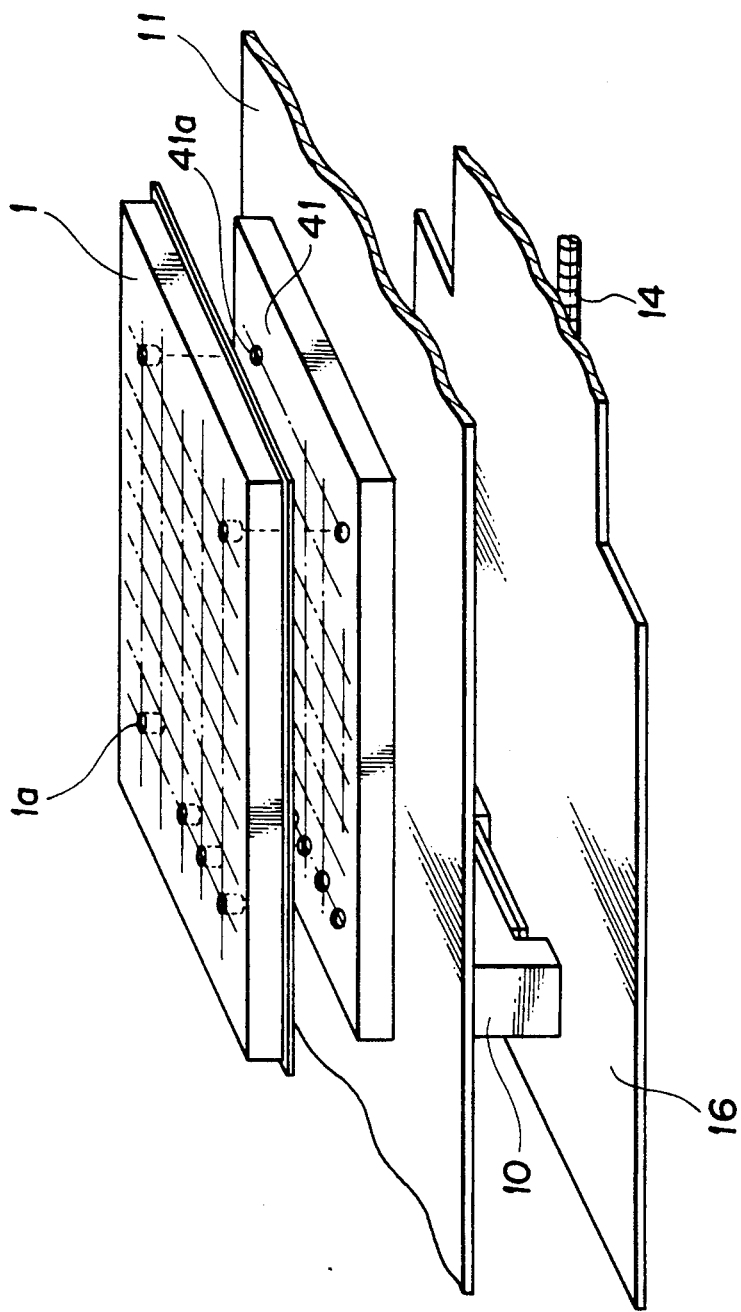
FIG. 15 is a view of the horizontal plate and an explanation showing the positional relationship between the windows and the reaction vessels.

As shown in FIG. 14, the horizontal top plate 11 mounts thereon the side support flanges 1c of the microplate 1, and the horizontal plate 11 has a raised plate part 41 which extends under and is generally parallel to plate 1b. This raised plate part 41 functions as a light preventing mask and has thereon a plurality of round holes 41a used as windows through which light passes. The round holes 41a correspond to and are aligned with the reaction vessels 1a of the microplate 1. The diameter of the round hole 41a is determined so as to permit a part of the conical bottom portion of the respective reaction vessel 1a to project downwardly into and through the round hole 41a with a small annular gap therebetween, when the microplate 1 is placed on the horizontal plate 11. Hole 41a is of slightly smaller diameter than the outer diameter of the reaction vessel 1a. The plate 41 is generally nontransparent to prevent transmission of light therethrough.

Other constructional features of this embodiment are the same as that of the second embodiment.

The third embodiment constructed as describe above has substantially the same function and effect as that of the second embodiment. In this third embodiment, because the tapered part of the bottom portion of the reaction vessel 1a mutually reacts with the respective round hole 41a, it is possible to prevent the microplate 1 from being mounted at an erroneous position without difficulties.

A fourth embodiment of the invention will be explained with reference to FIGS. 16–19. Corresponding parts of this embodiment are again identified by the same reference numbers used above.

Figure 21:
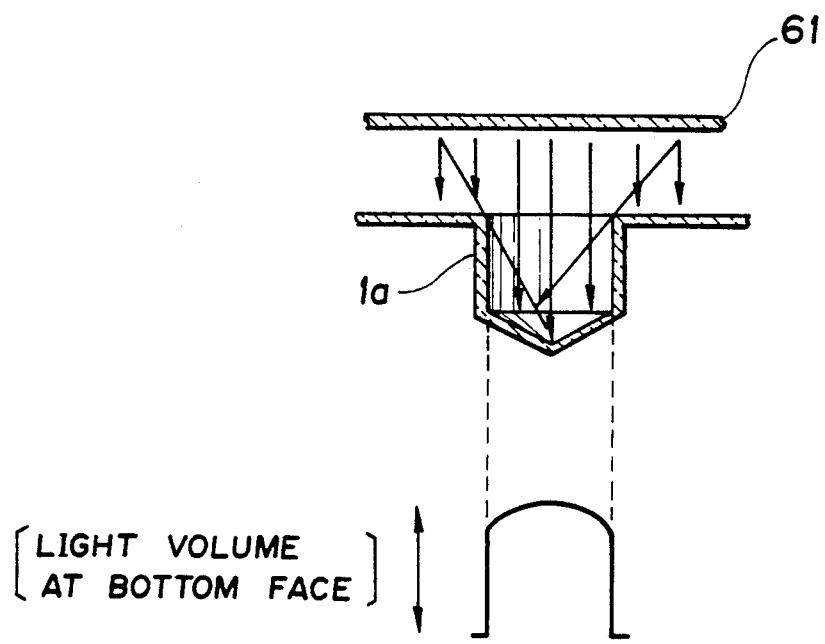
FIGS. 21-23 are explanations of functional aspects of the apparatus.
Figure 22A:
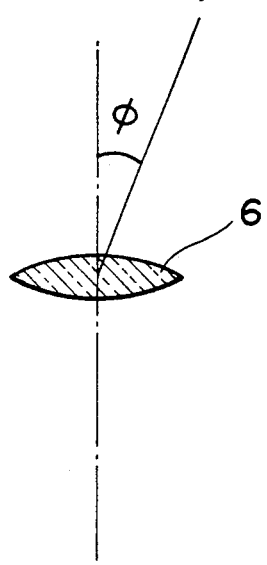
Figure 22B:
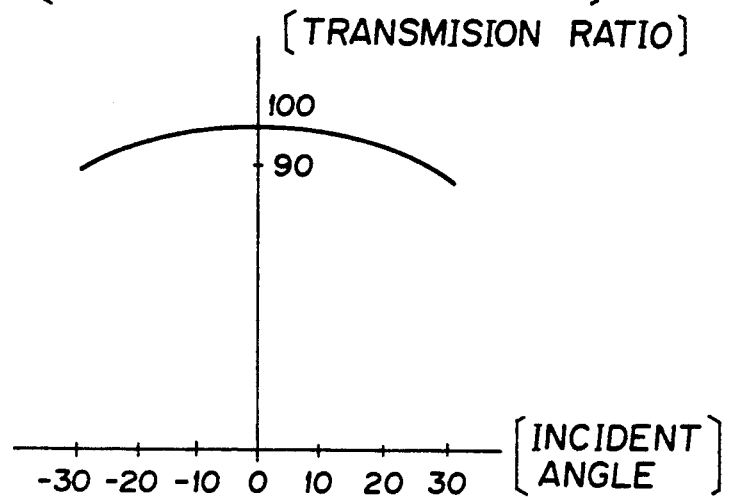
Figure 23:
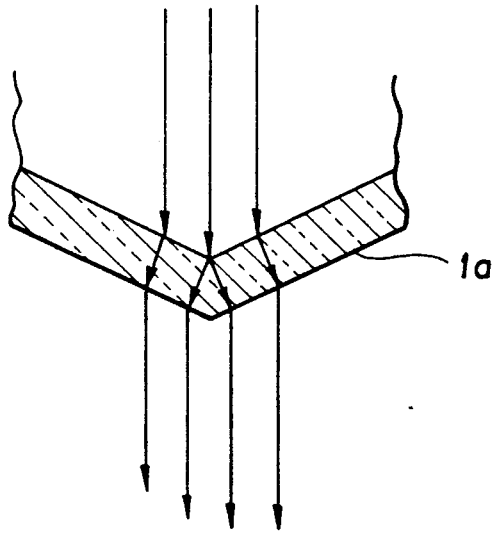

However, for background purposes, reference is first made to FIGS. 21–23. Normally the conical bottom face of the reaction vessel 1a is shone uniformly, so that the light volume at the central bottom portion of the reaction vessel 1a becomes the largest and it becomes rather non-enough at the peripheral portion of the vessel. As shown in FIGS. 22(a) and 22(b), the light transmission ratios differ according to the incident angle to the convex lens 6 and the pattern images projected on the primary CCD sensor essentially are bright at the central portion and becomes darker toward the peripheral portion according to the particular opening of the lens and some restriction on the focal distance, etc. Accordingly, the precision in reading function of the primary CCD sensor 7 is high at the central portion and low at the peripheral portion. On the contrary, practically, as shown in FIG. 23, some shadow is generated at the central bottom face of the reaction vessel 1a due to light refraction phenomenon and a shadow is detected in a shape of a nose N (FIG. 11) at the central bottom face as shown by the sensor output wave shape. It is possible to erroneously judge a vacant condition or non-agglutination state of the reaction vessel as an agglutination condition.

Figure 16:
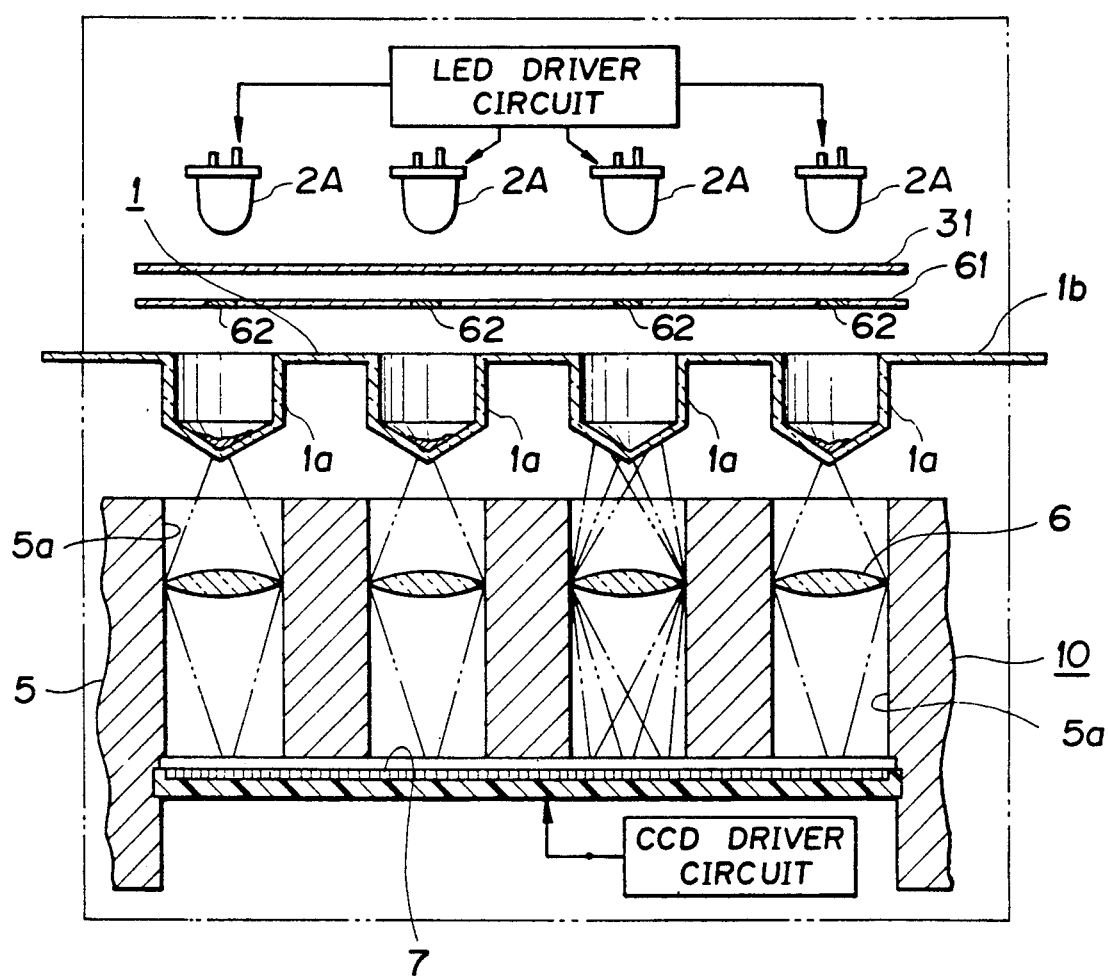
FIG. 16 is a concept view showing the structure of a fourth embodiment according to the invention.

According to the embodiment shown in FIG. 16, the immunological agglutination detecting apparatus has a microplate 1 of the agglutination examination plate consisting of the transparent base plate 1b and a number of reaction vessels 1a are formed thereon and arranged in a grid or matrix pattern, the vessels 1a having conical bottom faces, light emitting diodes 2A used as light emitting means are arranged at one side of the microplate 1 (on the upper side of FIG. 16), and the primary CCD sensor 7 used as light receiving means is arranged at the other side of the microplate 1. The microplate 1 is adapted to be mounted on the horizontal top plate (such as plate 11 in FIG. 6) constituting a part of the immunological agglutination detecting apparatus. The part of the horizontal plate 11, on which the microplate 1 is mounted, has an opening formed therein and the opening is adapted to be closed by the microplate 1.

Between the light emitting diodes 2A and the microplate 1, a light distribution plate 31 and an optical filter plate 61 are arranged so as to be in parallel with the microplate 1 with a fixed gap therebetween. The optical filter 61 has as seen in FIG. 15 light reducing portions 62 respectively arranged so as to face and be generally aligned with the central portions of respective reaction vessels 1a. These portions 62 permit less light to be transmitted therethrough than do the adjacent portions of the filter plate 61. The light distribution plate 31 and the optical filter 61 are integrally secured to the lower face of an upper plate (such as plate 17 in FIG. 6).

Figures 18A, 18B:
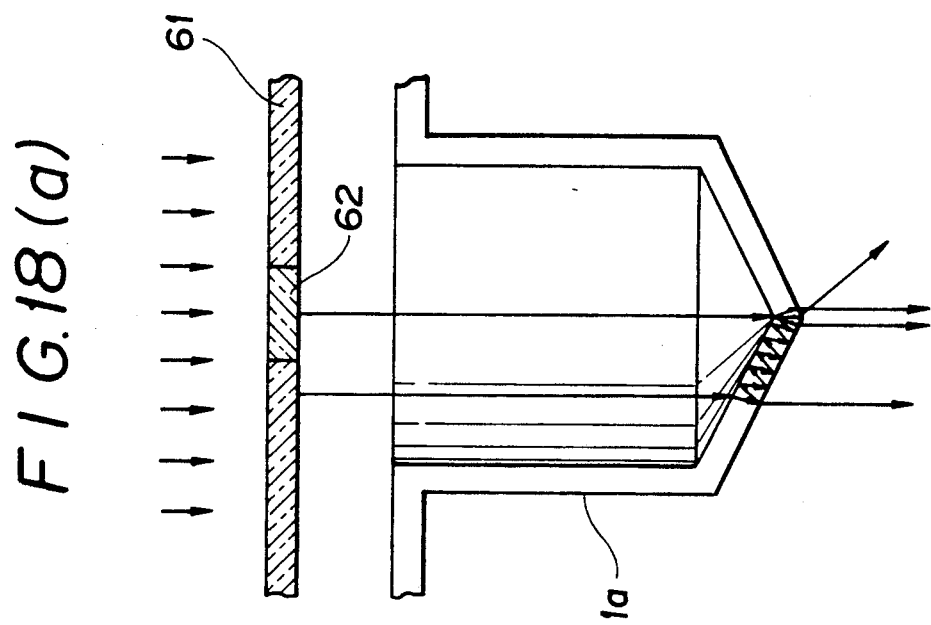
FIG. 18($a$) is an explanation of the condition in which the effect of the shadow generated by the light refraction phenomenon at the lowest point of the reaction vessel shown in FIG. 16 is restricted, and FIG. 18($b$) shows the output of the primary CCD sensor when the reaction vessel is vacant.

According to this embodiment of the invention, because the shining light from the light emitting diodes 2A passes through the light reducing portions 62 formed in the optical filter 61, light volume or intensity reaching the central portion of the bottom faces of respective reaction vessels 1a is lesser than that of the peripheral portion of the bottom faces as shown in FIG. 17(b). Due to light refraction at the bottom central portion of the reaction vessel 1a, some shadow is generated at the lowest bottom point. However, light volume reaching the peripheral portion of the bottom face of the reaction vessel is larger than that reaching the central portion, so that light at the peripheral portion diffusely reflects and the shadow at the central portion becomes weak. As a result, the sensor outputs the result as shown in FIG. 18(b) when the reaction vessel 1a is vacant. In this drawing, the dotted line shows the output of the sensor without the optical filter 61.

Figures 19A, 19B, 19C:
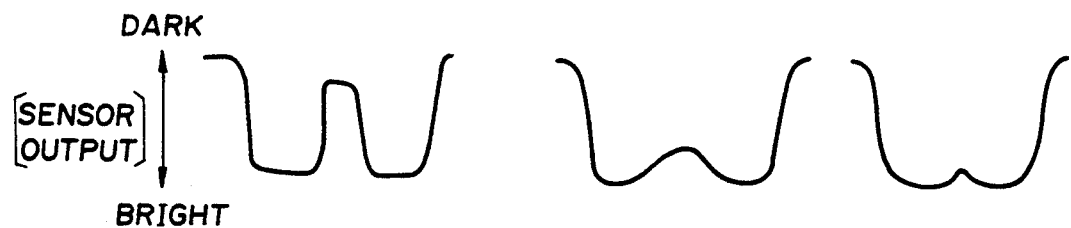
FIGS. 19($a$)-($c$), respectively show the output waves as the primary CCD sensor corresponding to the typical agglutination patterns obtained in the embodiment of FIG. 16.

FIGS. 19(a), 19(b) and 19(c), respectively show the outputs of the primary CCD sensor 7 corresponding to the typical agglutination patterns formed on the bottom faces of the reaction vessels 1a according to this embodiment. FIG. 19(a) shows the output from the sensor generated when no agglutination or condensation has occurred and blood cell corpuscles descend separately rolling down along the slant bottom face and being deposited around the center portion of the bottom portion of the vessel. FIG. 19(b) depicts the output obtained when the uniform deposit pattern as shown in FIG. 10 are obtained, and FIG. 19(c) shows the case in which there is no substance in the reaction vessel.

In operation, the output signals from the primary CCD sensor 7 are sent to the CPU (not shown) through the analog/digital convertor (not shown). In the CPU, the movement distance of the moving plate 16 is calculated by the feeding speed (R.P.M.) of the motor in order to determine the particular columns of reaction vessels under examination to automatically judge the agglutination patterns of the samples in respective reaction vessels.

According to this embodiment, with the optical filter 61 having light reducing portions 62 corresponding to the centers of respective reaction vessels 1a on the microplate 1, it is possible to make the illumination to the center of the bottom face of the respective reaction vessel 1a a little darker than that of the peripheral portion thereof. In consequence, the disadvantageous effect of the shadow generated at the lowest summit portion of the bottom face of the reaction vessel 1a can be restricted, improving preferably the precision of the examination of blood. It is noted that a set of light emitting diodes 2A and the primary CCD sensor 7 are fixed in their positional relationship and moved integrally as a unit, so that it is possible to further improve the examination precision. In addition, because the microplate 1 is fixed or of stationary type, the blood cell corpuscles agglutinated in the reaction vessels 1a and deposited on their bottom portions are not distributed or scattered due to vibration or the like, as a result it is possible to preferably keep the result of agglutination in a stable condition.

Figure 20:
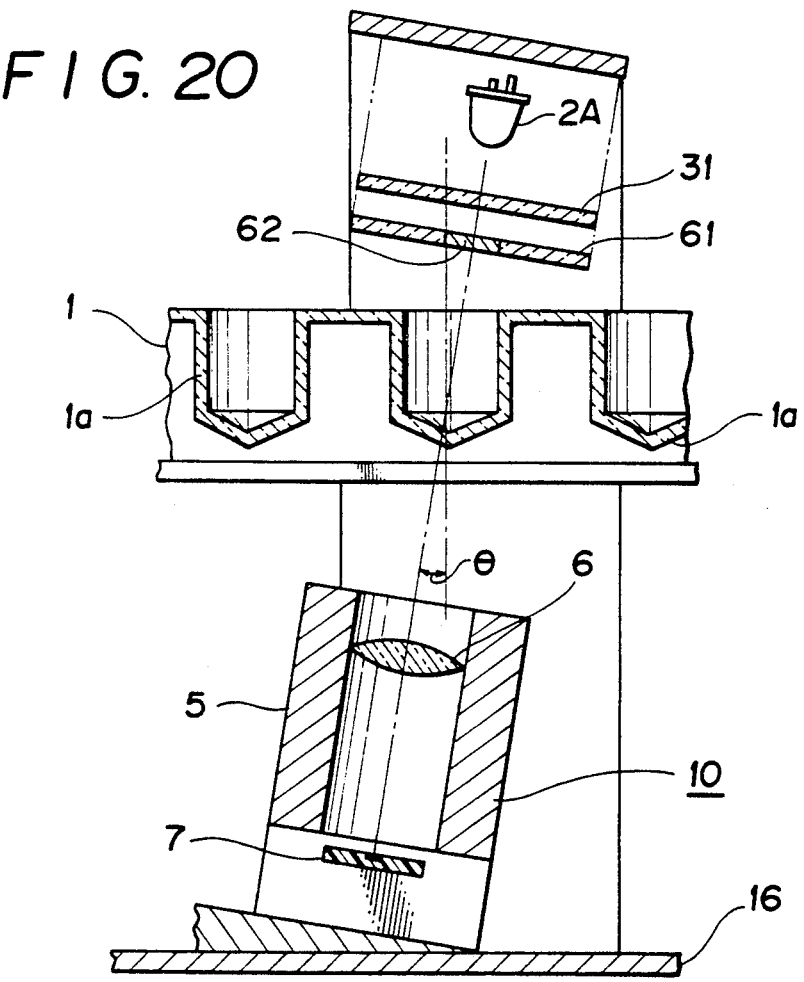
FIG. 20 is a concept view showing the construction of a fifth embodiment according to the invention.

Next, a fifth embodiment will be described with reference to FIG. 20. The constructional members of the fifth embodiment which are similar to that of the above embodiments will be referred to by the same reference numerals.

According to the fifth embodiment, on the moving plate 16 (FIG. 6), the light receiving unit 10 is mounted so as to be slanted by an angle $\theta$ from the vertical line and correspondingly the light emitting diodes 2A is slanted by an angle $\theta$ relative to the vertical. The light distribution plate 31 and the optical filter 61 are placed on planes perpendicular to the line connecting the centers of the light emitting diodes 2A and the convex lenses 6 installed in the light receiving unit 10. In consequence, it is possible to detect agglutination patterns obtained in places other than the centers of the reaction vessels. The construction of the fifth embodiment is otherwise substantially the same as that of the fourth embodiment.

The functional effect of the immunological agglutination detecting apparatus according to the fourth embodiment is substantially the same as that of the fifth embodiment. In addition, because substantially no effect of the shadow generated by light refraction at the lowest summits of the reaction vessels is created, it is advantageously possible to judge agglutination patterns at a higher precision.

As described above, when the optical filter including light reducing portions formed therein so as to face the centers of respective reaction vessels in the agglutination examination plate is placed between the light emitting means and the examination plate, it is possible to make or set illumination on the center of the bottom face of the reaction vessel to be a little darker or weaker than the peripheral portion of the bottom face due to the special effect of the optical filter. In consequence, it is possible to reduce or restrict any effect of light refraction due to the particular shape of the lowest summit of the reaction vessel, so that the immunological agglutination detecting apparatus is improved considerably in the examination precision of the blood cell corpuscles agglutination patterns.

Although a particular preferred embodiment of the invention has been disclosed in detail for illustrative purposes, it will be recognized that variations or modifications of the disclosed apparatus, including the rearrangement of parts, lie within the scope of the present invention.

CCD as used above means Charge Coupled Device which was invented Mr. Boyle and his fellow men of the U.S.A. Bell Laboratory in 1970, which is a semiconductor function element.

The embodiments of the invention in which an exclusive property or privilege is claimed are defined as follows:

1. In an immunological agglutination detecting apparatus comprising an agglutination examination plate provided with a plurality of reaction vessels each having a slanted bottom face, said vessels being arranged in a grid pattern, a light emitting means situated on one side of said agglutination examination plate, and a light receiving means situated on the other side thereof in order to focus respective images of the agglutination patterns formed at said bottom faces of said plurality of reaction vessels due to an illuminating light outputted from said light emitting means on a light receiving element which is part of said light receiving means by a set of lenses so as to detect said agglutination pattern by using a signal outputted from the focussing thereof, the improvement wherein:

said light emitting means includes a plurality of primary point light sources and means for supporting said primary point light sources in a row, means for positioning at least one of said primary point light sources in alignment with a respective said reaction vessel so as to face said reaction vessel, a plurality of supplemental point light sources, means for supporting at least one of said supplemental point light sources adjacent each end of the row of primary point light sources, and first light intensity adjusting means for (1) adjusting the intensities of said primary point light sources without altering the intensities of said supplemental point light sources and (2) adjusting the intensities of said supplemental point light sources without altering the intensities of said primary point light sources.

2. In an immunological agglutination detecting apparatus including an examination plate provided with a plurality of reaction vessels each having a slanted bottom surface for facilitating the formation of agglutination patterns therein, said reaction vessels being arranged in a grid pattern, a light emitting means and a light receiving means respectively positioned on opposite sides of said examination plate so that light from said light emitting means is directed onto the agglutination patterns contained in a first selected group of said reaction vessels to form images of the agglutination patterns which are received by said light receiving means, said light receiving means including a light receiving element and a plurality of lenses for focusing the images onto the light receiving element, and said light receiving element including means for producing an output electrical signal in response to the images input thereto, the improvement wherein:

said light emitting means includes a plurality of primary point light sources arranged in a first row and equal in number to the number of reaction vessels in said first selected group, said apparatus further including means for positioning said primary point light sources in respective alignment with the reaction vessels of said first selected group to permit each said primary point light source to directly illuminate the reaction vessel in association therewith, and said light emitting means further including at least first and second supplemental point light sources positioned respectively adjacent opposite ends of said first row of primary point light sources, and first light intensity adjusting means for (1) adjusting the intensities of said primary point light sources without altering the intensities of said supplemental point light sources and (2) adjusting the intensities of said supplemental point light sources without altering the intensities of said primary point light sources.

3. An apparatus according to claim 2, wherein said light intensity adjusting means comprises a plurality of separate control means, each of said control means being adapted for adjusting the intensity of one of said supplemental point light sources without altering the intensities of any of the remaining point light sources.

4. An apparatus according to claim 3, wherein each of said control means is adapted for adjusting the intensity of a selected number of said primary point light sources without altering the intensities of any of the remaining point light sources.

5. An apparatus according to claim 2, wherein said first and second supplemental point light sources are positioned to define respective extensions of said first row of primary point light sources.

6. An apparatus according to claim 5, wherein a third said supplemental point light source is arranged adjacent one said end of said first row of primary point light source, said third supplemental point light source being laterally offset from said first row of primary point light sources.

7. An apparatus according to claim 6, wherein said light emitting means includes a second row of said primary point light sources which is laterally offset from and extends generally parallel to said first row of primary point light sources, said primary point light sources of said second row being respectively alignable with a further group of said reaction vessel equal in number to the number of primary point light sources in said second row, said third supplemental point light source being positioned adjacent one end of said second row of primary point light sources to define an extension of said second row, and a fourth said supplemental point light source being positioned adjacent the other end of said second row to define another extension thereof.

8. In an immunological agglutination detecting apparatus including a row of reaction vessels adapted to house agglutination reactions therein, a light emitting means for emitting light onto and through said reaction vessels, a light sensitive means for receiving light emitted from said light emitting means, and means for supporting said row of reaction vessels between said light emitting means and said light sensitive means so that light passes from said light emitting means through said reaction vessels and onto said light sensitive means, the improvement wherein:

said light emitting means includes a plurality of primary point light sources arranged in a row and equal in number to the number of reaction vessels, a plurality of supplemental point light sources arranged so that first and second said supplemental point light sources are disposed respectively adjacent opposite ends of said row of primary point light sources, and first light intensity adjusting means for (1) adjusting the intensities of said primary point light sources without altering the intensities of said supplemental point light sources and (2) adjusting the intensities of said supplemental point light sources without altering the intensities of said primary point light sources; and said apparatus includes means for positioning said primary point light sources in respective alignment with said reaction vessels to permit each said primary point light source to directly illuminate the reaction vessel in respective alignment therewith.

9. An apparatus according to claim 8, wherein said light intensity adjusting means comprises a plurality of separate control means, each of said control means being adapted for adjusting the intensity of one of said supplemental point light source without altering the intensities of any of the remaining point light sources.

10. An apparatus according to claim 9, wherein each of said control means is adapted for adjusting the intensity of a selected number of said primary point light sources without altering the intensities of any of the remaining point light sources.

* * * * *

UNITED STATES PATENT AND TRADEMARK OFFICE
CERTIFICATE OF CORRECTION

PATENT NO. : 5 169 601
DATED : December 8, 1992
INVENTOR(S) : Masato OHTA et al It is certified that error appears in the above-identified patent and that said Letters Patent is hereby corrected as shown below:

On the title page, column 1, item 75; please include Yukinori Harada from Shizuoka, Japan as a co-inventor.

Signed and Sealed this

Twenty-third Day of November, 1993

Attest:

BRUCE LEHMAN

Attesting Officer

Commissioner of Patents and Trademarks